United States Patent [19]

Nettekoven

[11] Patent Number: 5,846,237
[45] Date of Patent: *Dec. 8, 1998

[54] INSULATED IMPLEMENT

[75] Inventor: William S. Nettekoven, Sandy, Utah

[73] Assignee: MegaDyne Medical Products, Inc., Draper, Utah

[ * ] Notice: The term of this patent shall not extend beyond the expiration date of Pat. No. 5,531,743.

[21] Appl. No.: 547,571

[22] Filed: Oct. 24, 1995

Related U.S. Application Data

[63] Continuation-in-part of Ser. No. 342,215, Nov. 18, 1994, Pat. No. 5,531,743.

[51] Int. Cl.$^6$ .................................................. A61B 17/39
[52] U.S. Cl. ................... 606/41; 606/45; 606/49
[58] Field of Search ............... 606/41–52, 1; 116/208

[56] References Cited

U.S. PATENT DOCUMENTS

| | | | |
|---|---|---|---|
| 1,916,722 | 7/1933 | Ende . | |
| 2,285,929 | 6/1942 | Jacobson | 116/208 |
| 3,261,388 | 7/1966 | Kovac et al. | 116/208 |
| 3,842,792 | 10/1974 | Souther | 116/208 |
| 5,084,045 | 1/1992 | Helenowski | 606/49 |
| 5,195,959 | 3/1993 | Smith | 604/34 |
| 5,228,478 | 7/1993 | Kleisle | 116/208 |
| 5,312,401 | 5/1994 | Newton et al. | 606/46 |
| 5,531,743 | 7/1996 | Nettekoven et al. | 606/49 |

FOREIGN PATENT DOCUMENTS

| | | |
|---|---|---|
| 2592575 | 11/1986 | France . |
| 2404764 | 9/1974 | Germany . |
| 8202488 | 8/1982 | WIPO . |
| 9202272 | 2/1992 | WIPO . |

Primary Examiner—Lee S. Cohen
Assistant Examiner—David M. Ruddy
Attorney, Agent, or Firm—John L. Sigalos

[57] ABSTRACT

An instrument wherein coatings of two different materials are disposed on external surfaces. The first of these coatings is selected to provide an insulating layer overlying at least a principal surface of the instrument, whereas the second is included to provide an indication of the likely remaining useful life of the insulating layer. The relative characteristics between the two coatings is selected so that when the visual appearance of the second coating progresses to a predetermined level, the insulating qualities of the first coating will still be satisfactory but approaching a point when the instrument has reached the end of its useful life, thus providing a ready and passive visual indication of the time when the instrument should be replaced.

28 Claims, 1 Drawing Sheet

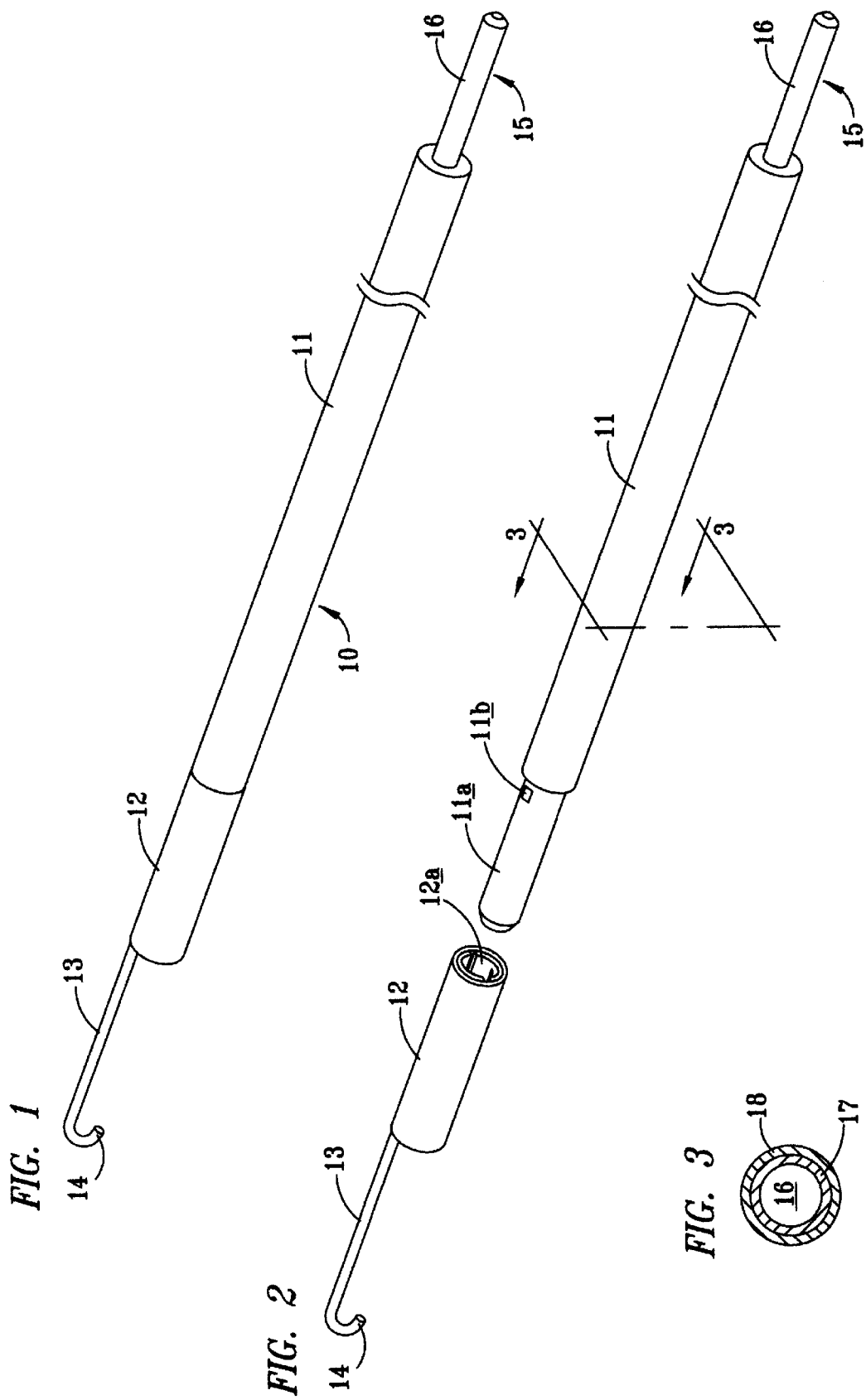

INSULATED IMPLEMENT

This is a Continuation-in-Part of U.S. patent application Ser. No. 08/342,215 filed Nov. 18, 1994 now U.S. Pat. No. 5,531,743 granted Jul. 2, 1996. It relates to insulating coatings and more particularly to such insulating coatings that are to be visually monitored to ensure maintenance of insulating integrity.

BACKGROUND OF THE INVENTION

As technology has progressed, there have arisen an increasing number of applications in which insulating coatings have been needed on surfaces of implements and other products. Thus, for example, in the field of medicine, there have been an increasing number of implements on certain of whose surfaces insulating coatings are needed. These include but are not limited to sophisticated implements for conducting both laparoscopic and non-laparoscopic procedures.

As is known to those skilled in the art, as surgical knowledge and techniques have progressed, there has been a corresponding trend toward size reduction of surgical incisions and invasive instruments, thus decreasing patient trauma and contributing to rapidity of patient recovery. This has led to the practice of laparoscopic and other surgical procedures using small medical electrodes. The incidence of AIDS and other highly dangerous or fatal communicable diseases has highlighted the importance of using either discardable components or of thoroughly sterilizing those that are used more than once. While thorough sterilization may be more economical and cost effective for certain types of implements, there are others in which the harsh environments of sterilization (e.g., autoclaving) may be excessively harmful or result in a reduction in useful life. Moreover, for some implements, repeated use itself may result in wear or deterioration. These considerations are applicable to both laparoscopic and non-laparoscopic environments.

In protecting against communication of disease, a variety of electrosurgical techniques and implements have heretofore been proposed, illustrative of which are those described in U.S. Pat. No. 1,916,722 granted to F. M. Ende Jul. 4, 1933; German Patent 2,404,764 granted to Bernard Weissman, et al. 19 Sep., 1974; PCT International Application US82/0084 filed by William S. Walker 25 Jan., 1982; and PCT International Application US 91/05520 filed by Edwin Langberg 2 Aug., 1991. According to proposals of these patents, multi-element implements have included reusable bodies with removable and disposable tips or electrodes. The main bodies or holders may be sterilized if needed and re-used, and the tips, blades or electrodes either discarded after one use or sterilized and re-used. However, there remain problems such as costs and time associated with sterilization and with optimization of use of the parts that make up an assembled instrument. For example, according to prior art proposals, the minimum expected useful life of an electrosurgical instrument has been identified and records kept of the length and type of use as well as the number of times the instrument has been sterilized, thus consuming time required to keep such records. Obviously, such procedures produce undesired overhead expense. In addition, where such an instrument is discarded after the expected minimum useful life has occurred, unless it is at the lower end of the "bell curve" of life expectancy, its remaining useful life, as well as the remaining useful lives of others of the instruments is not utilized, thus foreclosing use of remaining life of each individual instrument and leading to additional inefficiencies. Accordingly, there has continued to be a need for an improved way for monitoring insulating coatings on sophisticated equipment in general, and particularly electrosurgical instruments, including an inexpensive and dependable way of identifying individual wear or deterioration so as to permit optimum use of each individual device while identifying a point beyond which use should be discontinued.

BRIEF SUMMARY OF THE INVENTION

While the principles embodied herein are applicable to a wide rage of sophisticated equipments and devices, the invention is described in connection with a preferred embodiment of an improved electrosurgical assembly which, according to the invention hereof includes an electrode holder for a disposable member wherein a major surface or the entire exterior surface of the holder is coated with two coatings of different life expectancies. A first coating comprises the principal insulating coating for providing required electrical insulation and is characterized by exhibiting a relatively long life expectancy; whereas the second coating which may overlie at least a part of the first coating has a lesser life expectancy than that of the first coating and is used as a passive indicator of the remaining life of the first coating. Accordingly, when in use, a visual indication of the condition of the second coating provides a conservative indication of the likely remaining life of the first coating, i.e., the principal coating. In some embodiments in which at least a part of the second coating overlies at least a part of the first coating, making the coatings of different colors, e.g., black and white, red and white, will make it very apparent visually when a safe margin of remaining life for the first coating for each individual device has been reached, thus indicating the need for replacement. Moreover, by using different colors in an overlie, damage due to physical marring becomes readily evident as, for example, revelation of the underlying color through scratches, nicks and the like.

OBJECTS AND FEATURES OF THE INVENTION

It is one general object of the invention to improve monitoring of insulating coatings on sophisticated equipment.

It is another general object of the invention to facilitate monitoring of insulating coatings on electrosurgical implements.

It is another object of the invention to facilitate determination of remaining useful lives of such equipments and implements.

It is still another object of the invention to increase utilization of remaining useful lives of insulated electrosurgical implements.

It is yet another object of the invention to provide a passive way of visually determining the remaining life of each individual equipment or instrument.

Accordingly, in accordance with one feature of the invention, an insulating coating is positioned on one or more surfaces which need insulation, and another coating of material having a determinable life less than that of the insulating coating is positioned over or adjacent to a part of the insulating coating, thus providing a sacrificial coating whose condition provides a conservative indication of the remaining useful life of the insulating coating.

In accordance with another feature of the invention, an electrosurgical implement is constructed in a plurality of parts including an optionally disposable tip or blade attached to a doubly coated tip holding member, thereby facilitating repeated and safe use.

In accordance with another feature of the invention, the doubly coated tip holding member includes at least partly overlying coatings of different life expectancies, thus facilitating passive visual identification of the condition of such coatings.

In accordance with yet another feature of the invention, the coatings may be of different colors and in embodiments in which the sacrificial coating partly overlies the other, deterioration of the sacrificial coating may be readily detected when the color of the undercoating begins to show.

In accordance with still another feature of the invention, through the use of the foregoing visual identification with certain medical members, counting the number of times a medical holding member has been sterilized or subjected to other deterioration-producing events may be eliminated, thus increasing efficiency in use.

In accordance with yet a further feature of the invention, one of aforementioned coatings may be positioned over the other by shrink-wrapping, thus facilitating it positioning.

These and other objects and features of the invention will be apparent from the following detailed description, by way of example of a preferred embodiment, with reference to the drawing.

BRIEF DESCRIPTION OF THE DRAWING

FIG. 1 is a perspective view of an electrosurgical electrode according to the invention;

FIG. 2 is another perspective view of the electrosurgical electrode of FIG. 1 showing the separation of the blade or tip from the main body; and FIG. 3 is a section view taken along the lines 3—3 of FIG. 2.

DESCRIPTION OF A PREFERRED EMBODIMENT

Before proceeding to a detailed description, it may be helpful to consider the following definition of the word "Resposable".

As used herein, "Resposable" means a device in which a part such as a tip or blade is optionally disposable and in which a portion such as a holding member for the optionally disposable part is reusable.

Although the illustrative preferred embodiment herein described relates to a Resposable device, it should, as noted above, be emphasized that the principles transcend such and are also applicable to non-resposable, reusable medical instruments where there is concern that repeated use and resterilization can degrade the performance and utility thereof. This is especially true of electrosurgical electrodes where breaches in insulation integrity can cause harmful complications. Besides laparoscopic electrodes, this includes general surgery electrodes, OB/GYN electrodes, and the like.

Now turning to the drawing, and more particularly FIG. 1 thereof, it will be seen to be a perspective view of the electrosurgical blade according to the invention. There, a composite electrosurgical instrument is shown at 10. It includes a main body 11 which is a holder for detachable tip portion 12. As illustrated, tip portion 12 includes an extension 13 terminating in a curved hook 14. Of course, as will be evident to those skilled in the art, extension 13 could readily be a surgical blade or other surgical implement. At proximal end 15, there is included a conventional electrically conductive extension 16 which is provided for making conventional connections thereto.

Now turning to FIG. 2, the composite electrosurgical instrument of FIG. 1 is shown with detachable tip portion 12 detached. As will be evident to those skilled in the art, any of a variety of known ways may be employed to fasten the detachable tip 12 to the main body 11. However, in FIG. 2 there is illustrated the provision of distal extension 11a which is adapted for insertion into a corresponding chamber 12a provided within tip portion 12. A locking lug 11b is provided as shown and engages a corresponding recess (not shown) within chamber 12a to provide for securely locking tip portion 12 to main body 11.

As mentioned above, FIG. 3 is a sectional view taken along the section lines 3—3 of FIG. 2 and illustrates the preferred locations and relationships of the aforementioned two coatings that are identified 17 and 18. At this point it should be noted that while in accordance with the preferred embodiment both coatings are insulating, such is not essential to the practice of the invention. For example, although the under coating 17 should be insulating, the exterior coating 18 may be either essentially non-insulating or partially insulating in character so long as it changes in appearance with use as a function of the remaining life of the insulating coating 17 so that it represents a dependable visual indicator for the remaining life of the insulating coating 17. It should also be understood that although in the preferred embodiment, the exterior coating 18 completely covers the insulating undercoating on the main body 11, such is not a requisite for practicing the invention hereof.

Detachable tip 12 may be made of any of a variety of materials known by those skilled in the art to be suitable therefor. However, in the preferred embodiment hereof, such are seen to be silicone layer 19 overlying stainless steel portion 20 from which stainless steel extension 13 projects. Preferably covering extension 13 is a thin layer of fluorocarbon.

Although, as mentioned above, a variety of conductive and insulating materials may be employed for the main body 11 (for example, polyetherimide and polyvinylidene fluoride), the metallic portions are preferably comprised of stainless steel, the insulating coating 17 of polytetrafluoroethylene (PTFE, Teflon), and the coating 18 of polyolefin. These may be applied by a variety of techniques that are well known to those skilled in the art.

In practicing the invention, the main body, e.g., body 11, may be used and sterilized repeatedly as, for example, by autoclave. After each sterilization, it is examined visually for signs of insulation deterioration which, as mentioned above, become evident through a deterioration of coating 18. Although such deterioration can be visually observed without resort to use of particular coloration, by making the exterior and interior coatings of highly contrasting colors, identification of deterioration of the exterior coating will be facilitated and be dramatically evident through the presence of bleeding of the under color through that of the upper. In addition, nicks, scratches, abrasion and other discrete damage to the integrity of the insulation will also be dramatically evident.

It will now be evident that there has been described herein an improved combination of coatings providing for the passive progressive visual monitoring of the condition of electrical insulation thereon, and that it is easy and cost-effective to use, thus contributing to its attractiveness and desirability.

Although the invention hereof has been described by way of a preferred embodiment, it will be evident that other adaptations and modifications may be employed without departing from the spirit and scope thereof. Thus, the principles of the invention are deemed to have applicability to a wide range of implements and other products in addition to the particular preferred example set forth above. Examples thereof are other laparoscopic and non-laparoscopic instruments having insulating coatings.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. A medical implement having:
   (a) a principal surface;
   (b) an insulating coating disposed on said principal surface; and
   (c) another coating disposed adjacent to said insulating coating, said another coating being initially and continuously exposed and having a life expectancy less than that of said insulating coating, whereby visual inspection of said another coating discloses a condition when likely remaining life of said insulating coating is less than a dependable level.

2. A medical implement according to claim 1 wherein said insulating coating and said another coating are of different colors.

3. A medical implement according to claim 1 wherein a part of said another coating is disposed contiguous to said insulating coating.

4. A medical implement according to claim 1 wherein a part of said another coating directly overlies a part of said insulating coating.

5. A medical implement having a principal surface, an insulating coating disposed on said principal surface and another coating, characterized said another coating being initially and continuously exposed and in that said another coating is intentionally selected to have a useful life less than that of said insulating coating.

6. A medical implement according to claim 5 further characterized in that said insulating coating and said another coating are of different colors.

7. A medical implement according to claim 5 further characterized in that a part of said another coating is disposed contiguous to said insulating coating.

8. A medical implement according to claim 5 further characterized in that a part of said another coating directly overlies a part of said insulating coating.

9. A medical instrument comprising:
   (a) a member having an elongated body; said member having a principal exterior working surface;
   (b) A first layer of insulating material on said principal exterior working surface; and
   (c) A second layer of other material on said elongated body, said second layer being initially and continuously exposed and intentionally selected to have a lesser life expectancy than that of said insulating material and to exhibit its remaining life expectancy by changes in its visual appearance.

10. A medical instrument according to claim 9 in which said first layer essentially covers said principal exterior working surface.

11. A medical instrument according to claim 9 in which said second layer covers a part of said first layer.

12. A medical instrument according to claim 10 in which said second layer covers a part of said first layer.

13. A medical instrument according to claim 9 in which said second layer covers all of said first layer.

14. A medical instrument according to claim 10 in which said second layer covers all of said first layer.

15. A medical instrument according to claim 9 in which said second layer is insulating.

16. A medical instrument according to claim 10 in which said second layer is insulating.

17. A medical instrument according to claim 9 in which said elongated body is comprised of multiple parts.

18. A medical instrument according to claim 9 in which said elongated body includes two principal parts.

19. A medical instrument according to claim 9 in which said elongated body includes a detachable tip member and a main body attached to said detachable tip member.

20. A medical instrument according to claim 19 in which said principal exterior working surface is on a surface of said main body.

21. A medical instrument according to claim 9 wherein said first layer of insulating material is of a first color and said second layer of other material is of a different color.

22. A medical instrument according to claim 10 wherein said first layer of insulating material is of a first color and said second layer of other material is of a different color.

23. A medical instrument according to claim 11 wherein said first layer of insulating material is of a first color and said second layer of other material is of a different color.

24. A method of determining remaining life of an insulating coating on a medical instrument comprising:
   (a) disposing said insulating coating on a visibly accessible surface of said instrument;
   (b) providing another material having a lesser life expectancy than that of said insulating coating, the remaining life expectancy of said another material being evident from visual inspection;
   (c) disposing said another material on an initially and continuously visibly accessible surface of said instrument; and
   (d) periodically inspecting said another material on said visibly accessible surface to visibly ascertain its remaining life expectancy.

25. The method according to claim 24 wherein said step of disposing said another material on said visibly accessible surface of said instrument includes a step of shrink-wrapping said another material on said visibly accessible surface.

26. The method according to claim 24 further including forming said instrument in a plurality of parts including a disposable tip and a reusable main body; and wherein disposing said insulating coating includes a step of affixing said insulating coating to a working surface of said main body.

27. The method according to claim 26 wherein said step of disposing said another material on a visibly accessible surface of said instrument includes disposing said another material onto said insulating coating.

28. The method according to claim 26 wherein said step of disposing said another material on a visibly accessible surface of said instrument includes disposing said another material onto essentially all of said insulating coating.

* * * * *